United States Patent [19]

Wunderlich et al.

[11] Patent Number: 5,192,760
[45] Date of Patent: Mar. 9, 1993

[54] 3-CARBALKOXYAMINO-5-(ALPHA-AMINO-PROPIONYL)-5H-DIBENZ[B,F]AZEPINES AND METHOD FOR THEIR MAKING

[75] Inventors: Helmut Wunderlich, Dresden; Andreas Stark, Radebeul; Dieter Lohmann, Radebeul; Lothar Zenker, Radebeul; Reni Bartsch; Hildegard Poppe, both of Dresden, all of German Democratic Rep.; Aleksandr Petrovič Skoldinov, Moskau, U.S.S.R.; Natalja V. Kaverina, Moskau, U.S.S.R.; Anna Nikitična Grizenko, Moskau, U.S.S.R.; Valentin Viktorovič Lyskovzev, Moskau, U.S.S.R.; Ekaterina K. Grigoreva, Moskau, U.S.S.R.

[73] Assignee: Arzneimittelwerk Dresden GmbH, Radebeul, German Democratic Rep.

[21] Appl. No.: 546,375

[22] Filed: Jun. 29, 1990

[30] Foreign Application Priority Data

Jun. 30, 1989 [DD] German Democratic Rep. .................... 330175-3

[51] Int. Cl.$^5$ ................ A61K 31/55; C07D 223/18
[52] U.S. Cl. ................................... 514/217; 540/587
[58] Field of Search ................ 540/587; 514/217

[56] References Cited

FOREIGN PATENT DOCUMENTS 2493314 11/1980 France .
258224 3/1987 German Democratic Rep. .

Primary Examiner—Mukund J. Shah
Assistant Examiner—Matthew V. Grumbling
Attorney, Agent, or Firm—Schweitzer Cornman & Gross

[57] ABSTRACT

New 3-carbalkoxyamino-5-(alpha-aminopropionyl)-5H-dibenz[b,f]azepines of formula I and their pharmaceutically acceptable salts were found to be suitable actives for the treatment of cardiac arrhythmia. Previously unknown 3-carbalkoxyamino-5-(alpha-halogenpropionyl)-5H-dibenz[b,f]azepines are obtained from 3-carbalkoxyamino-5H-dibenz[b,f]azepines by reaction with alpha-halogenpropionyl halides. Through their reaction with ammonia, primary amines or secondary amines, the new 3-carbalkoxyamino-5-(alpha-aminopropionyl)-5H-dibenz[b,f]azepines are obtained, which can be optionally converted into their pharmaceutically acceptable acid addition salts.

2 Claims, No Drawings

3-CARBALKOXYAMINO-5-(ALPHA-AMINOPROPIONYL)-5H-DIBENZ[B,F]AZEPINES AND METHOD FOR THEIR MAKING

FIELD OF THE INVENTION

The invention relates to new 3-carbalkoxyamino-5-(α-aminopropionyl)-5H-dibenz[b,f]azepines, their pharmaceutically acceptable acid addition salts, and method for making.

BACKGROUND OF THE INVENTION

The new compounds of formula I have not been described previously either with respect to their synthesis or with respect to their pharmaceutical properties. The compounds of the present invention have substantial and decisive structural differences when compared to already known compounds with antiarrhythmic activity.

Various materials are known, for use in the therapy of heart disorders. These include, for example, quinidine, lidocaine, procainamide, mexiletin, disopyramide, mexiletin, disopyramide, propranolol and verapamil. Many of the known antiarrhythmic drugs exhibit unwanted adverse reactions and, in some case, insufficient efficacy for certain forms of arrhythmia. None of the known agents is entirely satisfactory, particularly for the for the long-term control of disordered heart activity. No generally valid rules can be defined which describe the structure-effect relationships, because the chemical structures of these various materials are very different. In particular, the therapeutic agents described show no obvious structural relationships to the compounds of the present invention.

The synthesis of lidocaine analogs is described in German Federal Republic accepted applications patent No. 2,235,745 and German Federal Republic published patent application No. 2,400,450. In particular, 2-amino-2',6'-propionoxylidide (tocainide) is named, which, in contrast to lidocaine, can also be administered orally. The structureS of these primary acylanalides are different from that of the compounds of the present invention.

Various 10-beta-dialkylaminopropionyl-2-carbalkoxyamino-phenothiazines are described in Soviet patent No. 332,835, which were shown to have antiarrhythmic, spasmolytic and other pharmacological effects. Preparations from this series, such as moracizine and ethacizine have become used in human medicine. A characteristic of this group of compounds is the phenothiazine ring, which tends to oxidize. The corresponding 5-sulfoxides are formed from these compounds due to the oxidation of the ring sulfur atom during storage and in the course of biological degradation. This weakening is progressive, until it is lost altogether. Therefore, the administration of drug forms of these materials has to be replaced at relatively short time intervals, to ensure the necessary blood levels.

The β-dialkylaminopropionyl group in the 10 position is a characterizing feature of the known therapeutic drugs. This further restricts their chemical stability, because, as is well known to those skilled in the art, this substitution is associated with a beta elimination of the dialkylamino group.

Beta elimination is a disadvantage also in the case of the 3-carbalkoxyamino-5-(beta-dialkylaminopropionyl)-10,11-dihydro-5H-dibenz[b,f]azepines, which are described in the German Democratic Republic patent No. 152,782, and in Soviet patent No. 1,089,089. Compared to the 3-carbalkoxyamino-5-dialkylaminoacetyl-10,11-dihydro-5H-dibenz[b,f]azepines, of the last mentioned patents, the compounds of the present invention have a variety of advantageous pharmacological effects. The strength and duration of action, the therapeutic breadth and the absorption behavior advantageously differentiate the compounds of the present invention from the known materials of the aforementioned prior art.

DESCRIPTION OF THE INVENTION

The present invention relates to a novel 3-carbolkoxyamino-5-(α-aminopropinonyl)-5H-dibenz[b.f]azepines of formula I

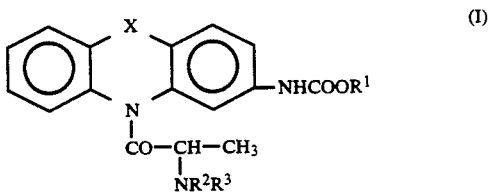

wherein
$R^1$ is a straight chain or branched $C_{1-3}$ residue
$R^2$ and $R^3$, which may be the same or different, in each case are hydrogen, a straight chain or branched or ring closed $C_{1-6}$ alkyl residue or β-oxyethyl group or
$R^2$ and $R^3$, together with a nitrogen atom to which they are linked, are a 5- or 6-membered heterocyclic ring, such as morpholine or piperidine, and
X is a —$CH_2$—$CH_2$—, or —CH=CH— residue
and to their pharmaceutically acceptable acid addition salts, and to methods for their synthesis. The compounds due to their antiarrhythmic effect, can be used in the case of heart disorders.

The compounds of the present invention can be synthesized in a simple manner, wherein known 3-carbalkoxyamino-5-H-dibenz[b,f]azepines are used as starting materials.

Pursuant to present invention the compounds of formula I can be obtained, by reacting a 3-carbalkoxyamino-5H-dibenz[b,f]azepine of formula II,

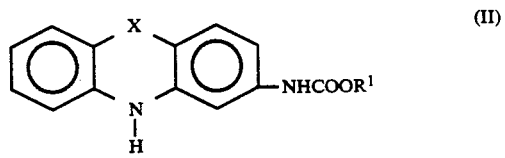

in which $R^1$ and X have the same meaning as above, with an α-halopropionyl halide of formula III,

in which Y and Z are chlorine or bromine, and reacting the resulting compound of formula IV,

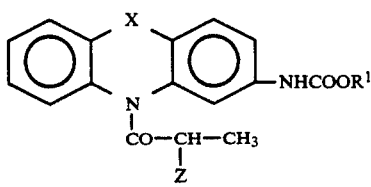

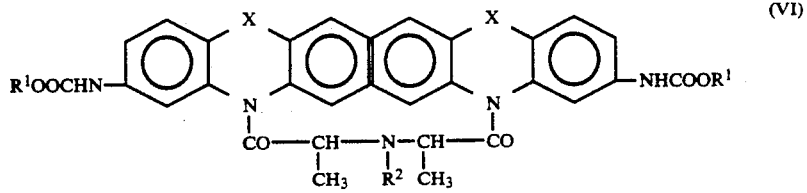

Such a use of amines has a particularly advantageous effect of largely suppressing a possible side reaction between a compound of formula I, on which $R^3$ is hydrogen, with a further molecule of alkyl halide of formula IV to form an undesired byproduct of formula VI, which is thus obtained, and in which $R^1$, Z and X have the same meaning as above, with an amine of formula V,

in which $R^2$ and $R^3$ have the same meaning as above.

The starting materials of the formulae II and III, required for the synthesis of compounds of formula IV, are known. When they are reacted, the new compounds of formula IV are formed.

For example, 3-carbethoxyamino-5-(α-bromopropionyl)-5H-dibenz[b,f]azepine is obtained from α-bromopropionyl chloride and 3-carbethoxyamino-5H-dibenz[b,f]azepine in an inert solvent, such as benzene, toluene, xylene, chlorobenzene, chloroform or dichloroethane, with hydrogen chloride being split off. The reaction can also be carried out in the presence of hydrogen halide acceptors, such as pyridine, triethylamine, sodium carbonate or potassium carbonate.

Pursuant to the invention, compounds of the formula IV are reacted with an amine of the formula V to form the compounds of the formula I. The amines of formula V that are required for this purpose, such as ammonia, methylamine, ethylamine, propylamine, dimethylamine, diethylamine, morpholine, and piperidine, are products that are readily available on an industrial scale. The reaction of the compounds of formula IV with an amine of formula V is suitably carried in solvents such as benzene, toluene, chlorobenzene, xylene, chloroform or low molecular weight alcohols at temperatures up to the boiling point of the solvent. It is also possible and, in some cases, of advantage, to carry out the reaction in the presence of water. In this case, it is advisable to use conventional commercial aqueous solutions of the corresponding amine reactants, such as aqueous ammonia, methylamine or ethylamine solutions. It may be of advantage for the optimum progress of the reaction to carry out the reaction under pressure, especially if the reactant of formula V is relatively volatile.

The reaction between a compound of formula IV and an amine of formula V can also be carried out in the presence of hydrogen halide acceptors. Potash, soda, tertiary amines and other amines, possibly in aqueous solution, are suitable as such hydrogen halide acceptors. Advantageously an excess of the amine of formula V, can be used as a hydrogen halide acceptor for the reaction. Suitably, 100% to 800% of amines are employed.

in which $R^1$, $R^2$ and X have the same meaning as above.

The inventive compounds of formula I are oily or crystalline bases, which can be optionally hydrated. By reaction with physiologically tolerated inorganic or organic acids, such as hydrochloric acid, sulfuric acid, tartaric acid, citric acid, etc., they can be converted into their acid addition salts, which can optionally be hydrated. The pharmaceutically acceptable salts are suitably used for the pharmaceutical processing of the inventive compounds of formula I. From the salts, the inventive bases of formula I can be recovered in a known manner, for example, by the action of alkaline reagents.

The new 5H-dibenz[b,f]azepines of formula I were found through animal experiments to have a pronounced antiarrhythmic effect. In various pharmacological models to test the antiarrhythmic effectiveness, the compounds of the present invention proved to be significantly more effective than lidocaine, mexiletin and morazicine, which are currently used in the therapy of heart disorders. In particular, compounds of the present invention show advantageous effects in comparison to the structurally related compounds, 10,11-dihydro-5H-dibenz[b,f]azepines, which are described in German Democratic Republic patent No. 152,782 and Soviet patent No. 1,089,089, of which 3carbethoxyamino-5-dimethylaminoacetyl-10,11-dihydro-5H-dibenz[b,f]azepine is currently undergoing clinical trials. There is even a significant improvement in the therapeutic breadth, as demonstrated by the aconitine model involving the rat (see Table 1, $Q_2 = LD_{50}$ iv./$ED_{73}$ iv.), while the tolerance is about the same and the effectiveness increased.

It is to be noted that the compounds of the present invention are well tolerated despite the presence of a tricyclic structure which is characteristic of a number of psychopharmaceutical drugs. In the case of the compounds of formula I neither sedating nor centrally exciting, or other emotionally unfavorable effects could be detected.

The compounds of formula I have in cases demonstrated a significantly improved absorption (see Table 1, $Q_1 = ED_{73\ po.}/ED_{73\ iv.}$). When the absorption ratio $Q_1$ is small, the amount of substance is reduced appreciably, which has to be contained in a tablet for oral administration.

Various pharmaceutical dosage forms can be employed, containing as actives the compound of the present invention, such as uncoated or coated tablets, drip solutions, injections, and others. Depending on the degree of severity of the heart disorder, the dosage, which can be administered once or several times daily, can vary on the average from about 5 to about 100 mg.

TABLE 1

| Test No. | X | $R^1$ | $R^2$ | $R^3$ | Aconitine (rat) $ED_{73}$ (mg/kg) iv. | Aconitine (rat) $ED_{73}$ (mg/kg) p.o. | $Q_1$ | Acute Toxicity (rat) $LD_{50}$ (mg/kg) iv. | $Q_2$ |
|---|---|---|---|---|---|---|---|---|---|
| 1 | $-CH_2-CH_2-$ | $C_2H_5$ | $CH_3$ | $CH_3$ | 2.4 (1.5–3.8) | 24 (16–36) | 10 | 20 (17–24) | 8 |
| 2 | $-CH_2-CH_2-$ | $C_2H_5$ | $C_2H_5$ | $C_2H_5$ | 1.3 (0.95–1.8) | 11 (9–13) | 9 | 12 (11–13) | 9 |
| 3 | $-CH_2-CH_2-$ | $C_2H_5$ | \multicolumn{2}{morpholino} | 47 (22–103) | to 80 K.W. | — | VP >70 | about 2 |
| 4 | $-CH_2-CH_2-$ | $C_2H_5$ | $CH_3$ | H | 0.12 (0.062–0.22) | 19 (10–34) | 158 | 12 (11–14) | 100 |
| 5 | $-CH_2-CH_2-$ | $C_2H_5$ | $C_2H_5$ | H | 0.16 (0.10–0.25) | 7 (6–8) | 44 | 9.3 (5.7–7.0) | 39 |
| 6 | $-CH_2-CH_2-$ | $C_3H_7$ (iso) | $CH_3$ | H | 0.55 (0.20–1.5) | 12 (6.4–22) | 22 | 21 (19–21) | 38 |
| 7 | $-CH_2-CH_2-$ | $C_3H_7$ (iso) | $C_2H_5$ | H | 0.33 (0.18–0.61) | 20 (12–31) | 61 | 10 (8.8–12) | 30 |
| 8 | $-CH_2-CH_2-$ | $CH_3$ | $CH_3$ | H | 0.86 (0.49–1.5) | 14 (8.9–23) | 16 | 24 (22–25) | 28 |
| 9 | $-CH_2-CH_2-$ | $CH_3$ | $CH_2-CH_2-OH$ | H | 4.0 | — | — | 55 | 14 |
| 10 | $-CH=CH-$ | $C_2H_5$ | $CH_3$ | H | 0.75 (0.43–1.3) | 4.9 (3.0–8.1) | 6.5 | 14 (13–15) | 19 |
| 11 | $-CH=CH-$ | $C_2H_5$ | $C_2H_5$ | H | 0.80 (2.4–6.9) | 14 | 18 | 14 (52–57) | 18 |
| 12 | $-CH_2-CH_2-$ | $C_2H_5$ | $C_3H_7(n)$ | H | 0.16 (0.058–0.43) | 3.5 (2.2–5.8) | 22 | 2.5 (2.2–2.8) | 16 |
| 13 | $-CH_2-CH_2-$ | $C_2H_5$ | H | H | 0.31 (0.21–0.45) | 14 (11–17) | 45 | 21 (19–23) | 68 |
| | Lidocain | | | | 9.2 (5.9–15) | — | — | 18 (17–21) | 2.0 |
| | Moracizin | | | | 1.1 (0.41–3.1) | 112 (28–445) | 102 | 11 (9.6–12) | 10 |
| | Bonnecor ® | | | | 0.28 (0.13–0.62) | 5.7 (1.6–20) | 20 | 11 (10–12) | 39 |
| | Mexiletin | | | | 15 (8.8–25) | 91 ($ED_{50}$ iv.) (58–143) | — | 41 (34–50) | 2.7 |

In Table I:

$ED_{73}$ iv. and po. are the dose in mg/kg, body weight which inhibits aconitine in female Wistar rats after iv. or po. administration of the test substance up to the occurrence of isolated ventricular extrasystolae. The procedure is also described by K. Femmer et al., in Pharmazie, vol. 31, page 36 (1976). The test substances are administered 2 minutes before the aconitine if given iv., and 60 minutes before the aconitine if given orally. The data is analyzed by the Probit regression analysis with a confidence interval of p=0.05 (values in parentheses).

$LD_{50}$ iv. is the lethal dose in mg/kg body weight for 50% of the experimental animals of an orientating acute toxicity test on male or female Wistar rats of our own breed, iv. administration in the tail vein, 3–4 dosages, 10 animals per group. Data analyzed by the Probit regression analysis with a confidence interval of p=0.05 (values in parentheses).

$Q_1$ is the ratio of $ED_{73\ po.}/ED_{73\ po.}$ to determine the absorption, and $Q_2$ is the ratio of $LD_{50\ iv.}/ED_{73\ iv.}$ to determine the therapeutic breadth.

The invention is further described with reference to the following illustrative examples.

EXAMPLE 1

3-Carbethoxyamino-5-(α-bromopropionyl)-10,11-dihydro-5H-dibenz[b,f]azepine(20.9 g, 0.05 moles) is suspended in 150 ml of 96% ethanol. An approximately 35% aqueous solution of methylamine (30 ml) is added and the mixture is stirred for 16 hours at 50° to 70° C. and then allowed to stand overnight at room temperature, with a fine crystalline deposit being obtained. This is filtered off with suction, washed twice with 25 ml portions of ethanol and dried at 100° C. 3-Carbethoxyamino-5-(α-methylaminopropionyl)-10,11-dihydro-5H-dibenz[b,f]-azepine (15 g), which can be purified further by stirring in acetone and recrystallizing from n-butanol and then melts at 201° to 203° C., is obtained.

The free base (10 g) is dissolved in 40 ml of methylene chloride. The pH is adjusted to a value of 2 with gaseous hydrochloric acid and the hydrochloride formed is precipitated by the addition of ethyl ether and filtered off with suction. 3-Carbethoxyamino-5-(α-methylaminopropionyl)-10,11-dihydro-5H-dibenz[b,f]azepine hydrochloride with a melting point of 168° C. is obtained.

The starting material can be synthesized as follows. 3-Carbethoxyamino-10,11-dihydro-5H-dibenz[b,f]azepine (28.2 g, 0.1 moles) is mixed with 300 ml toluene and 20 g (0.11 moles) of 2-bromopropionyl chloride and stirred for 4 hours on a boiling water bath, while HCl gas is escaping. The mixture is allowed to cool to room temperature and filtered and the filtrate is evaporated to dryness under reduced pressure. Upon addition of diethyl ether, the residue crystallizes, after temporarily going into solution. The crystalline deposit is filtered off with suction, washed with ether and dried. 3-Carbethoxyamino-5-(α-bromopropionyl)-10,11-dihydro-5H-dibenz[b,f]azepine (39 g) is obtained, which is purified by recrystallization from the 5-fold amount of isopropanol.

3-carbethoxyamino-5-(α-ethylaminopropionyl)-10,11-dihydro-5H-dibenz[b,f]azepine hydrochloride melting at 172° C. and 3-carbethoxyamino-5-(α-propylaminopropionyl)-10,11-dihydro-5H-dibenz[b,f]azepine hydrochloride melting at 177°-178° C. is synthesized in an analogous fashion.

EXAMPLE 2

3-Carbethoxyamino-5-(α-chloropropionyl)-10,11-dihydro-5H-dibenz[b,f]azepine(18.6 g) is suspended in a mixture of 200 ml aqueous ammonia solution and 250 ml of 96% ethanol, which had been saturated at room temperature with gaseous ammonia and stirred in a laboratory autoclave for 18 hours at 60° to 65° C. Subsequently, the solvent is driven off under reduced pressure at 70° C. The viscous residue is dissolved in dilute hydrochloric acid and the solution is treated with activated charcoal. It is made alkaline by the addition of concentrated ammonia solution and the so released base, is extracted with 100 ml of methylene chloride. After drying over sodium sulfate, the hydrochloride is precipitated with an ether solution of hydrogen chloride. 3-Carbethoxyamino -5-(α-aminopropionyl)-10,11-dihydro-5-dibenz[b,f]azepine hydrochloride is obtained, which melts at 193° to 195° C.

The starting material is prepared by a procedure similar to that of Example 1, whereby 3-Carbethoxyamino-5-(α-chloropropionyl)-10,11-dihydro-5H-dibenz[b,f]azepine with a melting point of 180° to 181° C. is obtained.

In an analogous manner there is prepared a compound 3-Carbethoxyamino-5-(α-methylaminopropionyl)-10,11-dihydro-5H -dibenz[b,f]azepine melting at 209° to 211° C. (ethanol).

EXAMPLE 3

3-Carbethoxyamino-5-(α-bromopropionyl)-5H-dibenz[b,f]-azepine (10 g) is mixed with 15 ml of approximately 35% aqueous methylamine solution and 75 ml of ethanol and heated in a laboratory autoclave for 12 hours at 90° to 95° C. After cooling to 4° C., the formed precipitate is filtered off with suction, mixed with 50 ml of acetone and then, again filtered off with suction and dried. 3-Carbethoxyamino-5-(α-methylaminopropionyl)-5H-dibenz[b,f]azepine (7 g) is obtained, which can be purified by being dissolved in dilute hydrochloric acid and precipitated with concentrated ammonia solution. The purified compounds melts at 217° to 219° C.

The starting material is synthesized by stirring 3-Carbethoxyamino-5H-dibenz[b,f]azepine (28 g, 0.1 moles) in 300 ml benzene and 20 g (0.11 moles) of 2-bromopropionyl chloride at the boiling point of the solvent. The reaction is completed after about 3 hours. The product is evaporated to dryness under reduced pressure and the viscous residue is washed with water. Crystallization commences due to the addition of ethyl ether. The crystalline material is filtered off with suction and recrystallized from the 3-fold amount of isopropanol. 3-Carbethoxy-5-(α-bromopropionyl)-5H-dibenz[b,-f]azepine (35 g), melting at 163° C., to 165° C., is obtained.

EXAMPLE 4

3-carbethoxyamino-5-(α-ethylaminopropionyl)-5H-dibenz[b,f]azepine is synthesized in a manner similar to that described in Example 3. The free base (6 g) is dissolved in ethyl ether and made acidic by the addition of isopropanolic hydrochloric acid. The hydrochloride formed becomes crystalline on being triturated with fresh ethyl ether. 3-Carbethoxyamino-5-(α-ethylaminopropionyl)-5H-dibenz[b,f]azepinehydrochloride, melting at 206° to 209° C., is obtained.

EXAMPLE 5

3-carbmethoxyamino-5-(α-bromopropionyl)-10,11-dihydro-5H-dibenz[b,f]azepine(4.0 g), 3.3 g (0.055 moles) of 2-aminoethanol and 70 ml of toluene are stirred for 6 hours at 100° to 110° C. The product is evaporated to dryness under reduced pressure, the residue washed with water and dissolved in dilute hydrochloric acid. The solution is purified with activated charcoal and the base is precipitated by making it alkaline with sodium hydroxide solution. The supernatant liquor is decanted off and the residue dissolved in acetone, from which the hydrochloride is precipitated by the addition of an ether solution of hydrogen chloride. 3-Carbmethoxyamino-5-(α-hydroxyethylamino-propionyl)-10,11-dihydro-5H-dibenz[b,f]azepine hydrochloride, melting at 163° to 164° C. with decomposition, is obtained.

The starting material is synthesized by refluxing 3-carbmethoxyamino-10,11-dihydro-5H-dibenz[b,f]azepine (13.5 g, 0.05 moles), 200 ml toluene and 12 g (0.06 moles) 2-bromopropionyl chloride for 5 hours and then cooling the mass, and the precipitated deposit is filtered off. After recrystallization from toluene, 14 g of 3-carbmethoxyamino5-(α-bromopropionyl)-10,11-dihydro-5H-dibenz[b,f]azepine, which melts at 158° to 159° C., are obtained.

We claim:

1. A compound of the formula

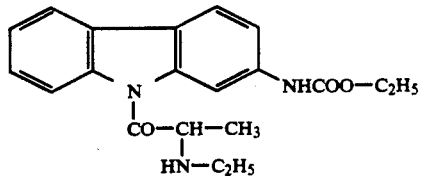

and its pharmaceutically acceptable acid addition salts.

2. A process for treating cardiac arrhythmia, which comprises administering to a patient in need thereof an effective dose of a pharmaceutical preparation containing as active ingredient the compound of claim 1.

* * * * *